(12) United States Patent
Zhan et al.

(10) Patent No.: US 7,192,702 B2
(45) Date of Patent: Mar. 20, 2007

(54) MODULATORS OF THE INTERACTION BETWEEN ARP2/3 AND CORTACTIN OR HS-1

(75) Inventors: Xi Zhan, Montgomery Village, MD (US); Takehito Uruno, Gaithersburg, MD (US)

(73) Assignee: University of Maryland, Baltimore, Baltimore, MD (US)

(*) Notice: Subject to any disclaimer, the term of this patent is extended or adjusted under 35 U.S.C. 154(b) by 566 days.

(21) Appl. No.: 10/362,827

(22) PCT Filed: Aug. 29, 2001

(86) PCT No.: PCT/US01/26834

§ 371 (c)(1),
(2), (4) Date: Feb. 27, 2003

(87) PCT Pub. No.: WO02/18626

PCT Pub. Date: Mar. 7, 2002

(65) Prior Publication Data

US 2004/0038323 A1  Feb. 26, 2004

Related U.S. Application Data

(60) Provisional application No. 60/228,894, filed on Aug. 30, 2001.

(51) Int. Cl.
*C12Q 1/68* (2006.01)
(52) U.S. Cl. .......................................................... 435/6
(58) Field of Classification Search ..................... 435/6
See application file for complete search history.

(56) References Cited

OTHER PUBLICATIONS

Cooper (1987, The Journal of Cell Biology 105:1473-1478).*
Fenteany and Zhu (2003, Current Topics in Medicinal Chemistry 3:593-616).*
Aspenström, P., et al., "Two GTPases, Cdc42 and Rac, bind directly to a protein implicated in the immunodeficiency disorder Wiskott-Aldrich syndrome," *Curr. Biol.* 6:70-75, Current Biology Ltd. (1996).
Blair, H. C., et al., "Osteoclastic Bone Resorption by a Polarized Vacuolar Proton Pump," *Science* 245:855-857, American Association for the Advancement of Science (1989).
Bowden, E. T., et al., "An invasion-related complex of cortactin, paxillin adn PKCµ associates with invadopodia at sites of extracellular matrix degradation," *Oncogene* 18:4440-4449, Stockton Press (Aug. 1999).
De Bruyn, P. P. H., et al., "The Migration of Blood Cells of the Bone Marrow through the Sinusoidal Wall," *J. Morphol.* 133:417-437, The Wistar Institute of Anatomy and Biology (1971).
Du, Y., et al., "Identification of a Novel Cortactin SH3 Domain-Binding Protein and Its Localization to Growth Cones of Cultured Neurons," *Mol. Cell. Biol.* 18:5838-5851, American Society for Microbiology (1998).
Egile, C., et al., "Activation of the CDC42 Effector N-WASP by the *Shigella flexneri* IcsA Protein Promotes Actin Nucleation by Arp2/3 Complex and Bacterial Actin-based Motility," *J. Cell Biol.* 146:1319-1332, The Rockefeller University Press (Sep. 1999).
Gallet, C., et al., "Tyrosine Phosphorylation of Cortactin Associated with Syk Accompanies Thromboxane Analogue-induced Platelet Shape Change," *J. Biol. Chem.* 274:23610-23616, The American Society for Biochemistry and Molecular Biology, Inc. (Aug. 1999).
Hiura, K., et al., "Differentiation Dependent Expression of Tensin and Cortactin in Chicken Osteoclasts," *Cell Motil. Cytoskeleton.* 30:272-284, Wiley-Liss, Inc. (1995).
Huang, C., et al., "Down-regulation of the Filamentous Actin Cross-linking Activity of Cortactin by Src-mediated Tyrosine Phosphorylation," *J. Biol. Chem.* 272:13911-13915, The American Society for Biochemistry and Molecular Biology, Inc. (1997).
Huang, C., et al., "The Role of Tyrosine Phosphorylation of Cortactin in the Locomotion of Endothelial Cells," *J. Biol. Chem.* 273:25770-25776, The American Society for Biochemistry and Molecular Biology, Inc. (1998).
Kapus, A., et al., "Cell Shrinkage Regulates Src Kinases and Induces Tyrosine Phosphorylation of Cortactin, Independent of the Osmotic Regulation of Na+/H+Exchangers," *J. Biol. Chem.* 274:8093-8102, The American Society for Biochemistry and Molecular Biology, Inc. (Mar. 1999).
Kim, L., and Wong, T. W., "Growth Factor-dependent Phosphorylation of the Actin-binding Protein Cortactin Is Mediated by the Cytoplasmic Tyrosine Kinase FER," *J. Biol. Chem.* 273:23542-23548, The American Society for Biochemistry and Molecular Biology, Inc. (1998).
Kitamura, D., et al., "Isolation and characterization of a novel human gene expressed specifically in the cells of hematopoietic lineage," *Nucl. Acids Res.* 17:9367-9379, IRL Press (1989).
Lechler, T., et al., "Direct Involvement of Yeast Type I Myosins in Cdc42-dependent Actin Polymerization," *J. Cell Biol.* 148:363-373, The Rockefeller University Press (Jan. 2000).

(Continued)

*Primary Examiner*—Susan Ungar
*Assistant Examiner*—Catherine Joyce
(74) *Attorney, Agent, or Firm*—Sughrue Mion, PLLC (57) ABSTRACT

The invention relates to methods for screening compounds for their ability to modulate actin polymerization. The invention is also related to compounds which modulate actin polymerization. More specifically, the invention is related to methods of screening compounds which modulate the interaction of cortactin or HS-1 with Arp2/3. The invention is also related to compounds which modulate the interaction of cortactin of HS1 with Arp2/3. Also provided are mutants of cortactin with decreased ability to interact with Arp2/3.

9 Claims, 8 Drawing Sheets

OTHER PUBLICATIONS

Li, Y., et al., "Tyrosine Phosphorylation of Cortactin Is Required for $H_2O_2$-mediated Injury of Human Endothelial Cells," *J. Biol. Chem.* 275:37187-37193, The American Society for Biochemistry and Molecular Biology, Inc. (Nov. 2000).

Liu, M., et al., "Mechanical Strain Induces pp60$^{src}$ Activation and Translocation to Cytoskeleton in Fetal Rat Lung Cells," *J. Biol. Chem.* 271:7066-7071, The American Society for Biochemistry and Molecular Biology, Inc. (1996).

Machesky, L.M., et al., "Scar, a WASp-related protein, activates nucleation of actin filaments by the Arp2/3 complex," *Proc. Natl. Acad. Sci. USA* 96:3739-3744, National Academy of Sciences (Mar. 1999).

Machesky, L.M., and Insall, R.H., "Scar1 and the related Wiskott-Aldrich syndrome protein, WASP, regulate the actin cytoskeleton through the Arp2/3 complex," *Curr. Biol.* 8:1347-1356, Current Biology Ltd. (1998).

Maruyama, S., et al., "Physical and Functional Association of Cortactin with Syk in Human Leukemic Cell Line K562," *J. Biol. Chem.* 271:6631-6635, The American Society for Biochemistry and Molecular Biology, Inc. (1996).

Mbalaviele, G., et al., "E-Cadherin Expression in Human Breast Cancer Cells Suppresses the Development of Osteolytic Bone Metastases in an Experimental Metastasis Model," *Cancer Res.* 56:4063-4070, American Association for Cancer Research (1996).

Miki, H., and Takenawa, T., "Direct Binding of the Verpolin-Homology Domain in N-WASP to Actin Is Essential for Cytoskeletal Reorganization," *Biochem. Biophys. Res. Commun.* 243:73-78, Academic Press (1998).

Mullins, R.D., "How WASP-family proteins and the Arp2/3 complex convert intracellular signals into cytoskeletal structures," *Curr. Opin. Cell. Biol.* 12:91-96, Elsevier Science (Feb. 2000).

Mullins, R.D., and Pollard, T.D., "Structure and function of the Arp2/3 complex," *Curr. Opin. Struct. Biol.* 9:244-249, Elsevier Science (Apr. 1999).

Mullins, R.D., et al., "The interaction of Arp2/3 complex with actin: Nucleation, high affinity pointed end capping, and formation of branching networks of filaments," *Proc. Natl. Acad. Sci. USA* 95:6181-6186, National Academy of Sciences (1998).

Okada, T., et al., "A novel *in vitro* assay system for transendothelial tumor cell invasion: significance of E-selectin and $\alpha_3$, integrin in the transendothelial invasion by HT1080 fibrosarcoma cells," *Clin. Exp. Metastasis* 12:305-314, Rapid Communications of Oxford Ltd. (1994).

Ohoka, Y., and Takai, Y., "Isolation and characterization of cortactin isoforms and a novel cortactin-binding protein, CBP90," *Genes to Cells* 3:603-612, Blackwell Science (1998).

Okamura, H., and Resh, M.D., "p80/85 Cortactin Associates with the Src SH2 Domain and Colocalizes with v-Src in Transformed Cells," *J. Biol. Chem.* 270:26613-26618, The American Society for Biochemistry and Molecular Biology, Inc. (1995).

Rohatgi, R., et al., "The Interaction between N-WASP and the Arp2/3 Complex Links Cdc42-Dependent Signals to Actin Assembly," *Cell* 97:221-231, Cell Press (Apr. 1999).

Schuuring, E., "The involvement of the chromosome 11q13 region in human malignancies: *cyclin D1* and *EMS1* are two new candidate oncogenes—a review," *Gene* 159:83-96, Elsevier Science B.V. (1995).

Schuuring, E., et al., "The Product of the *EMS1* Gene, Amplified and Overexpressed in Human Carcinomas, Is Homologous to a v-src Substrate and Is Located in Cell-Substratum Contact Sites," *Mol. Cell. Biol.* 13:2891-2898, American Society for Microbiology (1993).

Stevenson, B.R., et al., "Identificatiion of ZO-1: A High Molecular Weight Polypeptide Associated with the Tight Junction (Zonula Occludens) in a Variety of Epithelia," *J. Cell Biol.* 103:755-766, The Rockefeller University Press (1986).

Takemoto, Y., et al., "LckBP1, a proline-rich protein expressed in haematopoietic lineage cells, directly associates with the SH3 domain of protein tyrosine kinase p56$^{lck}$," *EMBO J.* 14:3403-3414, Oxford University Press (1995).

Uruno, T., et al., "Activation of Arp2/3 complex-mediated actin polymerization by cortactin," *Nature Cell Biol.* 3:259-266, Macmillan Magazines Ltd. (Mar. 2001).

Welch, M.D., et al., "The Human Arp2/3 Complex Is Composed of Evolutionarily Conserved Subunits and Is Localized to Cellular Regions of Dynamic Actin Filament Assembly," *J. Cell Biol.* 138:375-384, The Rockefeller University Press (1997).

Winter, D., et al., "Activation of the yeast Arp2/3 complex by Bee1p, a WASP-family protein," *Curr. Biol.* 9:501-504, Elsevier Science (May 1999).

Wu, H., et al., "Identification and Characterization of a Novel Cytoskeleton-Associated pp60$^{src}$ Substrate," *Mol. Cell. Biol.* 11:5113-5124, American Society for Microbiology (1991).

Wu, H., and Parsons, J.T., "Cortactin, an 80/85-Kilodalton pp60$^{src}$ Substrate, Is a Filamentous Actin-binding Protein Enriched in the Cell Cortex," *J. Cell Biol.* 120:1417-1426, The Rockefeller University Press (1993).

Yarar, D., et al., "The Wiskott-Aldrich syndrome protein directs actin-based motility by stimulating actin nucleation with the Arp2/3 complex," *Curr. Biol.* 9:555-558, Elsevier Science (May 1999).

Zhan, X., et al., "Murine Cortactin Is Phosphorylated in Response to Fibroblast Growth Factor-1 on Tyrosine Residues Late in the $G_1$ Phase of the BALB/c 3T3 Cell Cycle," *J. Biol. Chem.* 268:24427-24431, The American Society for Biochemistry and Molecular Biology, Inc. (1993).

* cited by examiner

MODULATORS OF THE INTERACTION BETWEEN ARP2/3 AND CORTACTIN OR HS-1

CROSS REFERENCE TO RELATED APPLICATIONS

This application is a 371 U.S. National Stage Entry of PCT application US2001/026834, filed Aug. 29, 2001, which, in turn, claims priority, pursuant to 35 U.S.C. § 119(e), to U.S. provisional patent application No. 60/228,894, filed Aug. 30, 2000, all of which are incorporated herein by reference.

STATEMENT REGARDING FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention relates to methods for screening compounds for their ability to modulate actin polymerization. The invention is also related to compounds which modulate actin polymerization. More specifically, the invention is related to methods of screening compounds which modulate the interaction of cortactin or HS-1 with Arp2/3. The invention is also related to compounds which modulate the interaction of cortactin or HS1 with Arp2/3. Also provided are mutants of cortactin with decreased ability to interact with Arp2/3.

2. Related Art

Amplification of the chromosome 11q13 constitutes an important genetic mechanism to progression of a subset of cancers, including breast cancer and head and neck carcinomas (Schuuring, E. D., et al., *Mol. Cell Biol.* 13:2891–2898 (1993)). The amplification often results in overexpression of cortactin, a filamentous actin (F-actin) associated protein. (Wu, H., et al., *Mol. Cell Biol.* 11:5113–5124 (1991); Zhan, X., et al., *J. Biol. Chem.* 268:24427–24431 (1993)). While overexpression of cortactin is usually correlated with poor prognosis (Schuuring, E., *Gene* 159:83–96 (1995)), presumably due to enhanced metastasis, the biochemical and biological functions of cortactin remain unclear.

Cortactin is a prominent substrate for several non-receptor protein tyrosine kinases, including Src, Fer and Syk (Wu, H., et al., *Mol. Cell Biol.* 11:5113–5124 (1991); Maruyama, S., et al., *J Biol. Chem* 271:6631–6635 (1996); Kim, L., and Wong, T. W., *J. Biol. Chem.* 273:23542–23548 (1998); Gallet, C., et al., *J. Biol. Chem.* 274:23610–23616 (1999)). Tyrosine phosphorylation of cortactin is a common cellular response to growth factors, stress, cell shrinkage, and cell injury mediated by reactive oxygen radicals (Zhan, X., et al., *J. Biol. Chem.* 268:24427–24431 (1993); Liu, M., et al., *J. Biol. Chem.* 271:7066–7071 (1996); Kapus, A., et al., *J. Biol. Chem.* 274:8093–8102 (1999); Li, Y., et al., (in press)). In vitro, tyrosine phosphorylation mediated by Src decreases the F-actin cross-linking activity of cortactin. (Huang, C., et al., *J. Biol. Chem.* 272:3911–13915 (1997)).

Figure 1A:
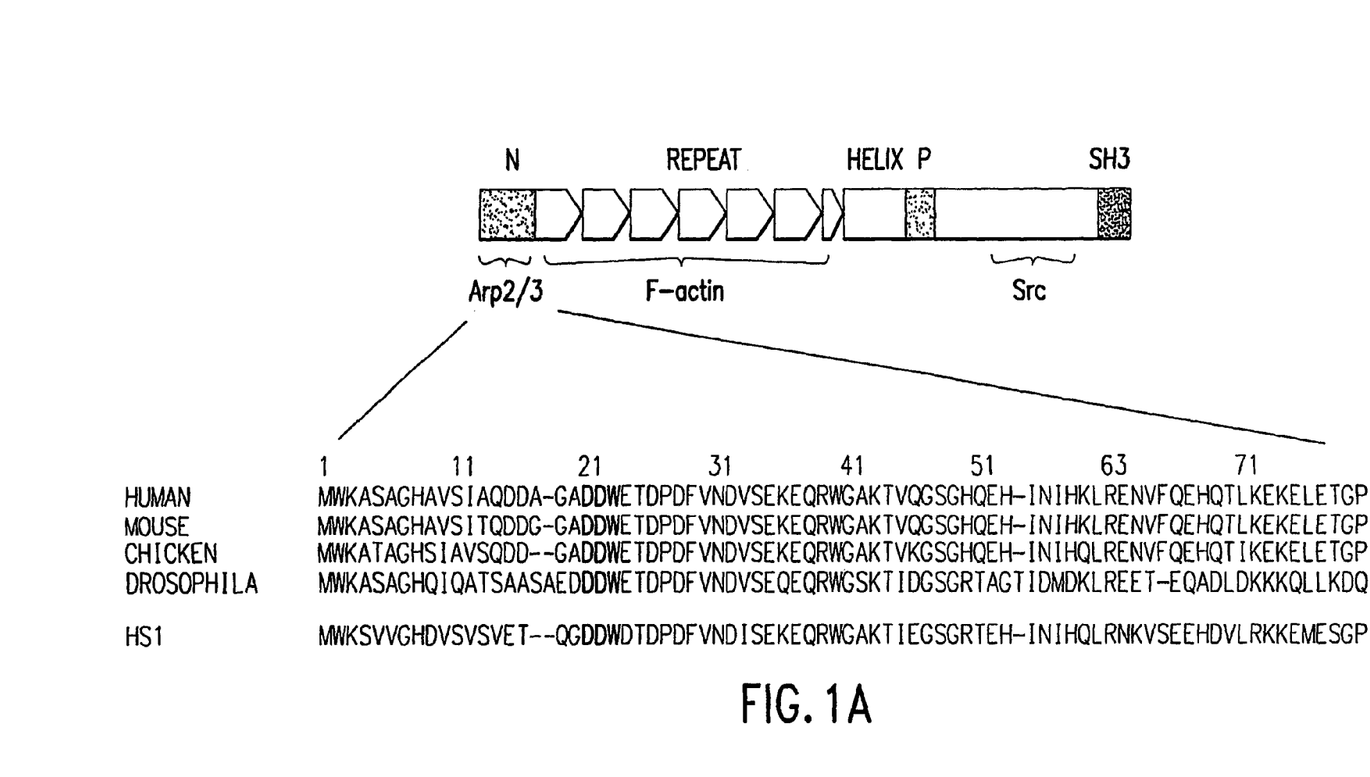
FIG. 1A shows a schematic presentation of the structural domains of cortactin. The domains that are targeted by Arp2/3 complex, F-actin and Src are labeled. The N-terminal amino acid sequence of human cortactin from 1 to 80 was compared to mouse, chicken and drosophila cortactin and human HS1.

Cortactin has a unique structure featured by six and one half tandem repeats of 37-amino-acid sequence and a carboxyl terminal SH3 domain (FIG. 1A). Between the repeat and the SH3 domain there are a proline-rich sequence, an alpha helical region and three tyrosine residues that are targeted by Src-related kinases (Huang, C., et al., *J. Biol. Chem.* 273:25770–25776 (1998)). In addition, cortactin contains an N-terminal domain, which is conserved across species and in HS1, a cortactin-related protein that is exclusively expressed in the hematopoietic lineage (Kitamura, D., et al., *Nucleic. Acids. Res.* 17:9367–9379 (1989)).

In cultured fibroblasts, cortactin is mainly distributed within cell leading edges such as lamellipodia and punctate-like structures (Wu, H., et al., *Mol. Cell Biol.* 11:5113–5124 (1991); Huang, C., et al., *J. Biol. Chem.* 273:25770–25776 (1998)). In MDA-MB-231 cells, an invasive breast cancer cell line, cortactin is associated with invadopodia, cortical structures that penetrate into and degrade extracellular matrix during invasion (Bowden, E. T., et al., *Oncogene* 18:4440–4449 (1999)).

SUMMARY OF THE INVENTION

The invention relates to methods for screening compounds for their ability to modulate actin polymerization. The invention is also related to compounds which modulate actin polymerization.

More specifically, the invention is related to screening compounds which modulate the interaction of cortactin or HS1 with Arp2/3. The invention is also related to compounds which modulate the interaction of cortactin or HS1 with Arp2/3.

The invention provides methods for treating diseases by administering compounds which modulate actin polymerization and/or modulate the interaction of cortactin or HS1 with Arp2/3. The invention further provides compositions which modulate actin polymerization and/or modulate the interaction of cortactin or HS1 with Arp2/3.

The invention also provides mutants of cortactin which have decreased ability to interact with Arp2/3.

BRIEF DESCRIPTION OF THE FIGURES

FIG. 1.

FIG. 2. FIG. 2A shows the interaction of cortactin with Arp2/3 complex in vivo. NIH 3T3 cell lysates were immunoprecipitated by either a cortactin monoclonal antibody and protein G-Sepharose (lane 1) or protein G-Sepharose alone (lane 2). The presence of Arp3, a subunit of Arp2/3 complex, in the cortactin pellets was detected by immunoblotting with an Arp3 polyclonal antibody. The position of Arp3 at approximately 50 kDa was indicated by an arrow (lane 1). (The major band shown in lanes 1 and 2 is background resulting from the cross-activity of the Arp3 antibody to protein G-Sepharose). Lane 3, a positive control for Arp3 (purified Arp2/3 complex).

FIG. 3.

FIG. 4.

FIG. 6.

FIG. 7. FIG. 7 presents an analysis of bone metastases of MDA-MB-231 cells in nude mice.

DETAILED DESCRIPTION OF THE PREFERRED EMBODIMENTS

Cortactin, a filamentous actin associated protein and a prominent substrate of Src, is implicated in breast tumor progression via gene amplification at chromosome 11q13. However, the function of cortactin remains obscure. The inventors have discovered, for the first time, that cortactin binds directly to Arp2/3 complex and activates Arp2/3 complex to promote actin polymerization in a manner independent of WASP-related proteins. The inventors have also discovered that the interaction of cortactin with Arp2/3 complex occurs at an N-terminal domain rich in acidic amino acids. Mutations at a conserved amino acid sequence of DDW abolished the interaction with Arp2/3 complex as well as the activation of Arp2/3 complex. A cortactin mutant deficient in binding to Arp2/3 complex fails to locate within membrane particulate structures of MDA-MB-231 breast cancer cells. These findings indicate a role of the interaction of cortactin with Arp2/3 complex in the actin polymerization associated with dynamic particulate structures, which have been implicated in tumor invasion and proteolysis of extracellular matrix.

The invention therefore provides a method of determining whether a test compound modulates the interaction of cortactin or HS-1 with Arp2/3 comprising a. contacting monomeric or polymeric actin, cortactin or HS-1, and Arp2/3 with a test compound; and b. detecting an alteration in the interaction of cortactin or HS-1 with Arp2/3 when compared with the interaction of cortactin or HS-1 with Arp2/3 in the absence of said test compound, wherein an alteration in the interaction of cortactin or HS-1 with Arp2/3 indicates that said test compound is a modulator of the interaction of cortactin or HS-1 with Arp2/3.

As used herein, "test compound" means any compound, including both (a) compounds which are known to modulate the interaction of cortactin or HS-1 with Arp2/3, and (b) compounds which are not known to modulate the interaction of cortactin or HS-1 with Arp2/3.

The distribution pattern of cortactin within cells is very similar to that of Arp2/3 (Welch, M. D., et al., *J. Cell Biol.* 138:375–384 (1997)), a protein complex composed of seven subunits that plays a critical role in the nucleation of actin polymerization (Mullins, R. D., *Curr. Opin. Cell Biol.* 12:91–96(2000)). The full activity of Arp2/3 complex requires its association with WASP family proteins, which are activated upon binding to membrane-associated small GTPases such as Cdc42. (Aspenstrom, P., et al., *Curr. Biol.* 6:70–75 (1996); Machesky, L. M., et al., *Proc. Natl. Acad. Sci. USA* 96:3739–3744 (1999); Winter, D., et al., *Curr. Biol* 9:501–504 (1999); Yarar, D., et al., *Curr. Biol* 9:555–558 (1999); Egile, C., et al., *J. Cell Biol.* 146:1319–1332 (1999); Rohatgi, R., et al., *Cell* 97:221–231 (1999)).

Within cells, cortactin exclusively associates with the cortical actin and is translocated to lamellipodia and membrane ruffles in response to stimulation. Cortactin's expression is nearly ubiquitous, except for in hematopoietic cells, where HS-1, a cortactin related protein, is expressed. The failure to knock out cortactin in mice indicates that cortactin is essential for embryonic development. Conversely, overexpression of cortactin is a frequent event in cancers including breast cancer, head and neck squamous carcinoma. Subjects with high levels of cortactin expression have poor prognosis and have higher metastasized tumors.

Figure 2A:
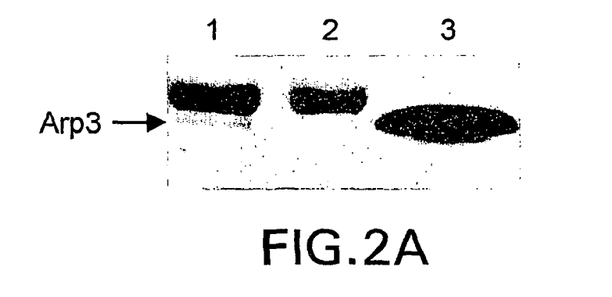

To test the possibility that cortactin directly interacts with Arp2/3 complex, the interaction of cortactin with Arp2/3 complex was examined by immunoprecipitation analysis. The lysate derived from NIH 3T3 cells was precipitated with a cortactin-specific antibody followed by immunoblotting with an antibody against Arp3, a component in Arp2/3 complex (Mullins, R. D., and Pollard, T. D., *Curr. Opin. Struct. Biol.* 9:244–249 (1999)). The immunoblot analysis detected an Arp3-related band only in the pellet derived from the cortactin antibody but not from the mock reaction (FIG. 2A). The apparent association of cortactin with Arp2/3 complex might be due to an indirect interaction because both cortactin and Arp2/3 complex can bind to F-actin. (Wu, H., and Parsons, J. T., *J. Cell Biol.* 120:1417–1426 (1993); Mullins, R. D., et al., *Proc. Natl. Acad. Sci USA* 95:6181–6186 (1998)). However, this possibility was unlikely because recombinant cortactin was able to interact readily with purified Arp2/3 complex in the absence of F-actin (FIG. 2B, lane 2).

Figure 1B:
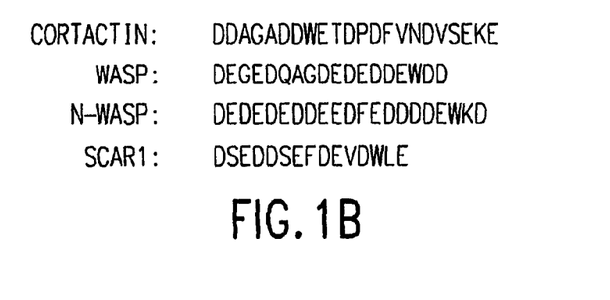
FIG. 1B shows a comparison of an acidic sequence in the N-terminus of murine cortactin with Arp2/3 complex binding domains of other WASP-related proteins. The conserved Trp was bolded.
Figure 2B:
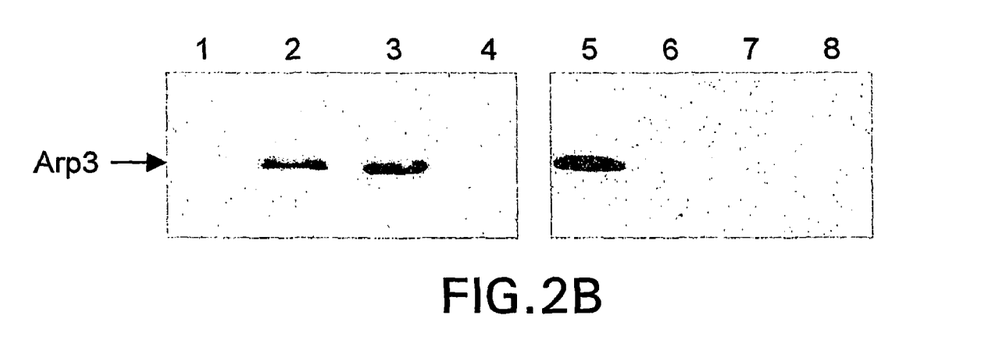
FIG. 2B shows the interaction of recombinant cortactin proteins with purified Arp2/3 complex by incubation of recombinant GST-cortactin with purified bovine Arp2/3 complex. The resulting protein complexes were precipitated with glutathione-Sepharose and further immunoblotted with an Arp3 antibody. Lane 1, GST-CortΔ (1–38); lane 2, GST-cortactin; lane 3, GST- CortΔSH3; lane 4, GST; lane 5, GST-Cort(1–39); lane 6, GST-Cort(1–39); lane 7, GSTCort(D20G/D21A); and lane 8, GST-Cort(W22A).
Figure 3:
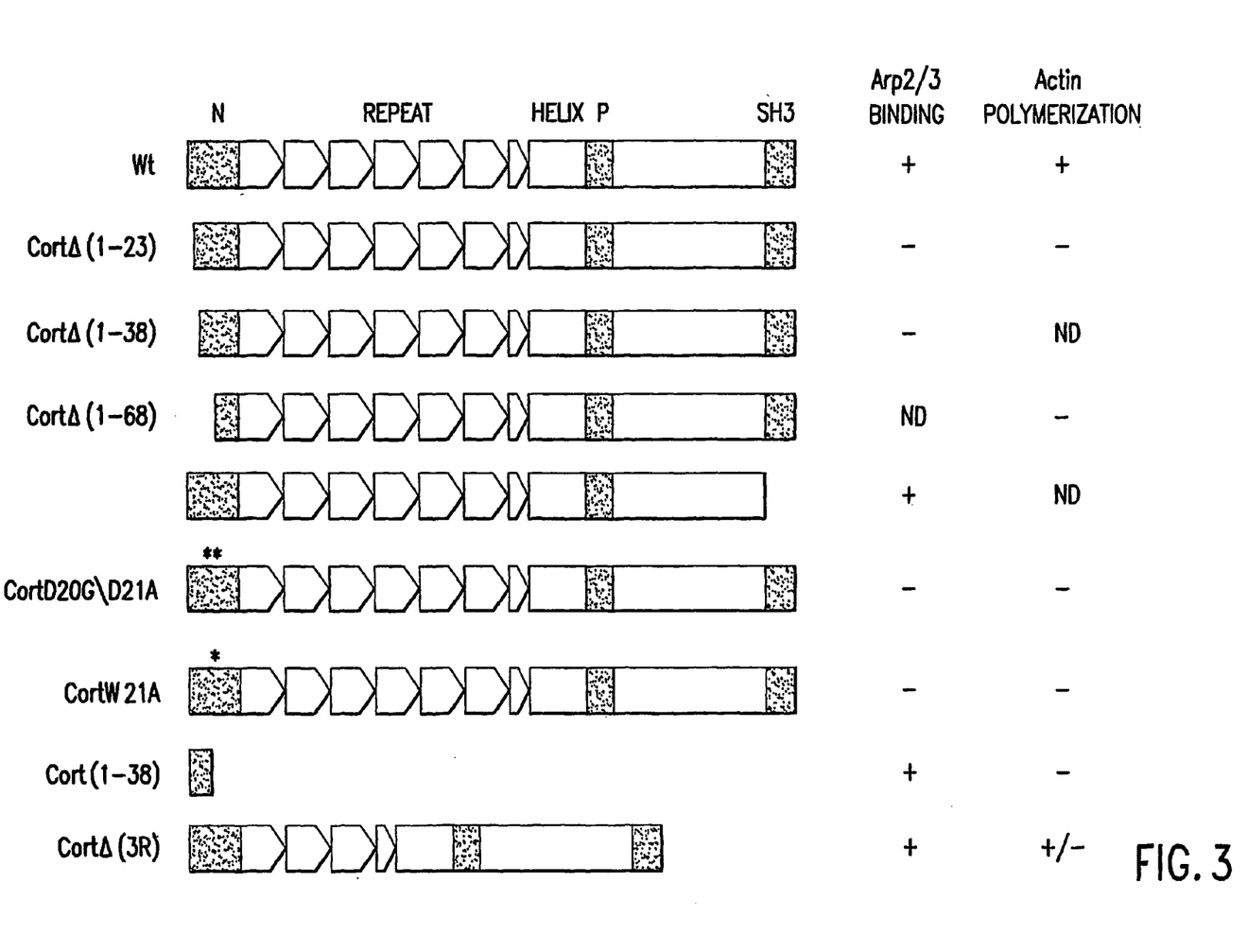
FIG. 3 lists a schematic summary of the analysis of the activity of a series of cortactin mutants for Arp2/3 complex binding and stimulation of actin polymerization.

By analyzing a series of deletion mutants in an in vitro actin polymerization assay, it was determined that the N-terminus of cortactin (amino acids 1 to 38) was essential and sufficient to bind to Arp2/3 complex (FIGS. 2 and 3). The N-terminus is remarkably conserved crossing species from human to Drosophila as well as in HS1 (FIG. 1A). This sequence is rich in acidic amino acids and contains a Trp residue. The similar amino acid composition is also found within the C-terminal domains of WASP-related proteins (FIG. 1B). To test whether these acidic amino acids and the Trp residue were important for cortactin to bind to Arp2/3 complex, Asp(20) and Asp(21) were mutated to Gly and Ala, and Trp(22) was mutated to Ala, respectively. As summarized in FIG. 4, both mutations abolished the interaction with Arp2/3 complex. Because acidic amino acids and the Trp residue in the Arp2/3 complex binding domain of WASP family proteins are important for their functions (Lechler, T., et al., *J. Cell Biol.* 148: 363–373 (2000)), this data suggests that cortactin binds to Arp2/3 complex in a similar manner as WASP-related proteins.

Figure 4A:
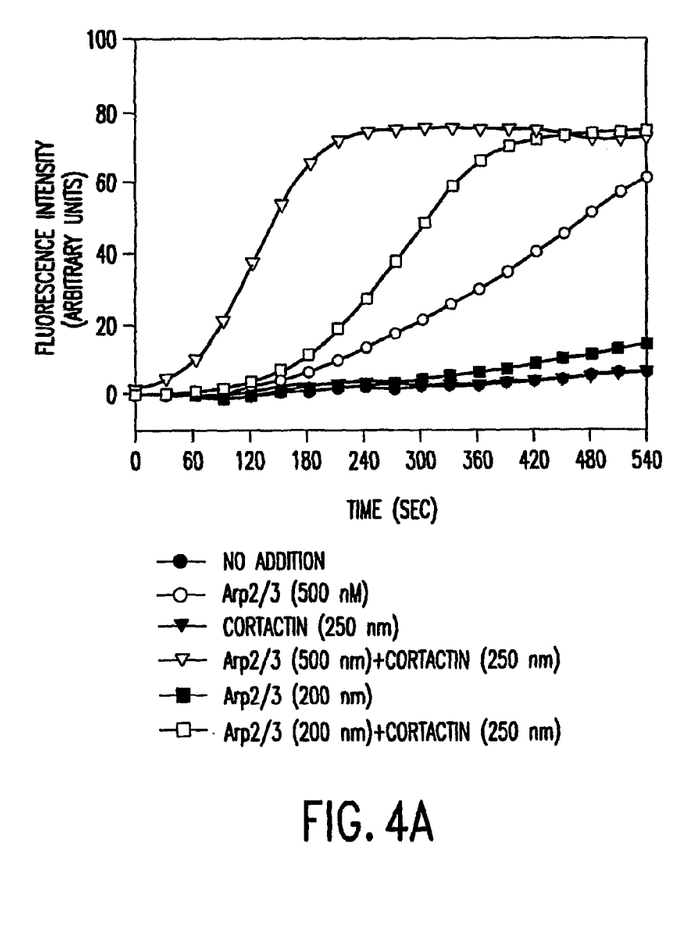
FIG. 4A shows a time course of actin polymerization measured by increase in fluorescence of polymerized pyrene actin, demonstrating the effect of cortactin on the actin polymerization nucleated by the Arp2/3 complex.
Figure 4B:
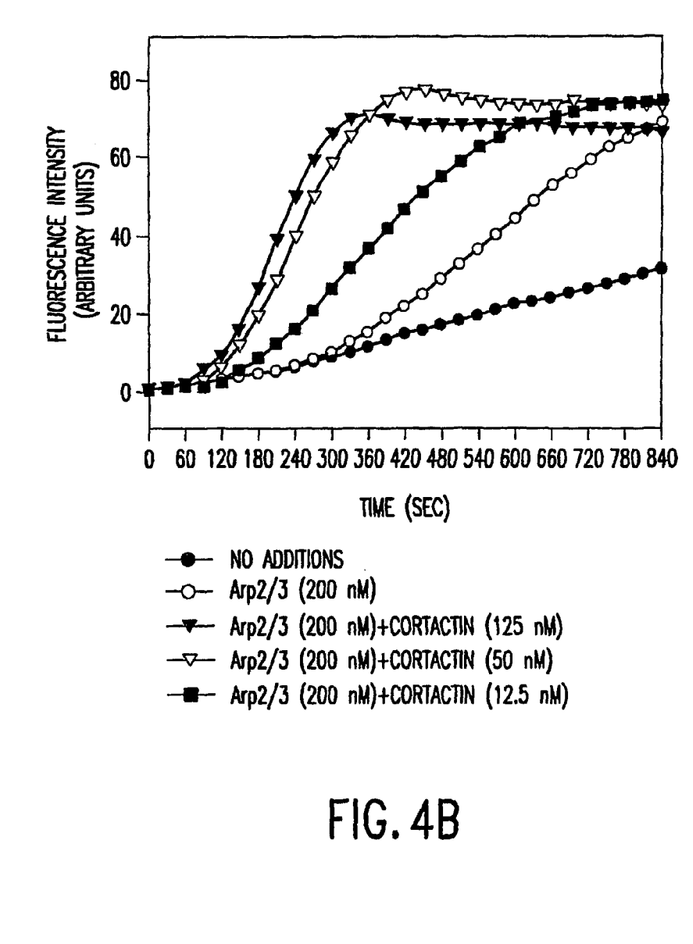
FIG. 4B shows the dose dependence of cortactin mediated actin polymerization.

The effect of cortactin on the activity of Arp2/3 complex was examined in more detail using the in vitro actin polymerization assay with pyrene-labeled monomeric actin. Cortactin alone had no apparent effect on the spontaneous actin polymerization, which is consistent with our previous report (Huang, C., et al., *J. Biol. Chem.* 272:3911–13915 (1997)), whereas Arp2/3 complex alone increased moderately the rate of actin polymerization (FIG. 4A). However, combination of Arp2/3 complex and cortactin reduced significantly the initial lag of actin polymerization. The half time to reach a steady state of actin polymerization in the presence of both Arp2/3 complex and cortactin was approximately 120 seconds, which was significantly less compared to 420 seconds in the presence of Arp2/3 complex alone and 30 minutes with actin alone (Rohatgi, R., et al., *Cell* 97:221–231 (1999)). The activity of cortactin for actin polymerization is also dependent on the concentration of Arp2/3 complex. The cortactin-mediated actin polymerization came to a saturated level within approximately 200 seconds in the presence of 500 nM Arp2/3 complex, whereas it required 450 seconds to plateau in the presence of 250 nM Arp2/3 complex. Cortactin also activated Arp2/3 complex in a dose dependent manner with a maximal activity at 50 nM under the condition where the actin polymerization was carried out in the presence of 2.5 μM actin and 200 nM Arp2/3 complex (FIG. 4B).

The activity of cortactin for actin assembly requires its ability to bind to Arp2/3 complex because mutants with deletion of sequences essential for binding to Arp2/3 complex failed to activate Arp2/3 complex (FIG. 3). However, binding to Arp2/3 complex itself seems not sufficient to stimulate actin polymerization. A peptide with the amino acids from 1 to 39, which was able to bind efficiently to Arp2/3 complex, was unable to stimulate actin polymerization (FIG. 3). Notably, a cortactin mutant containing only three repeats had 50% less affinity for F-actin compared to the intact cortactin (Wu, H., and Parsons, J. T., *J. Cell Biol.* 120:1417–1426 (1993)) and exhibited only approximately half activity of the intact form to activate Arp2/3 complex-mediated actin polymerization (FIG. 3). Thus, cortactin requires both activities binding to F-actin and Arp2/3 complex to increase the rate of actin polymerization. WASP family proteins require an actin-binding domain (WH2) as well as the acidic domain to activate Arp2/3 complex (Machesky, L. M., and Insall, R. H., *Curr. Biol.* 8:1347–1356 (1998)). However, the repeat domain of cortactin is distinct from the WH2 domain of WASP, the latter has a strong affinity for monomeric actin but not for F-actin. (Machesky, L. M., and Insall, R. H., *Curr. Biol.* 8:1347–1356 (1998); Miki, H., and Takenawa, T., *Biochem. Biophys. Res. Commun.* 243:73–78(1998). In contrast, the repeat domain of cortactin binds along the side of F-actin (Ohoka, Y., and Takai, Y., *Genes Cells* 3:603–612 (1998)). Therefore, it is possible that cortactin activates actin polymerization by enhancing the association of Arp2/3 complex on the side of existing filaments (Machesky, L. M., et al., *Proc. Natl. Acad. Sci. USA* 96:3739–3744 (1999)). Because the N-terminal domain and the repeat domain of cortactin are highly conserved in HS1, HS1 has a similar activity as cortactin to activate Arp2/3 complex-mediated actin assembly.

Figure 5:
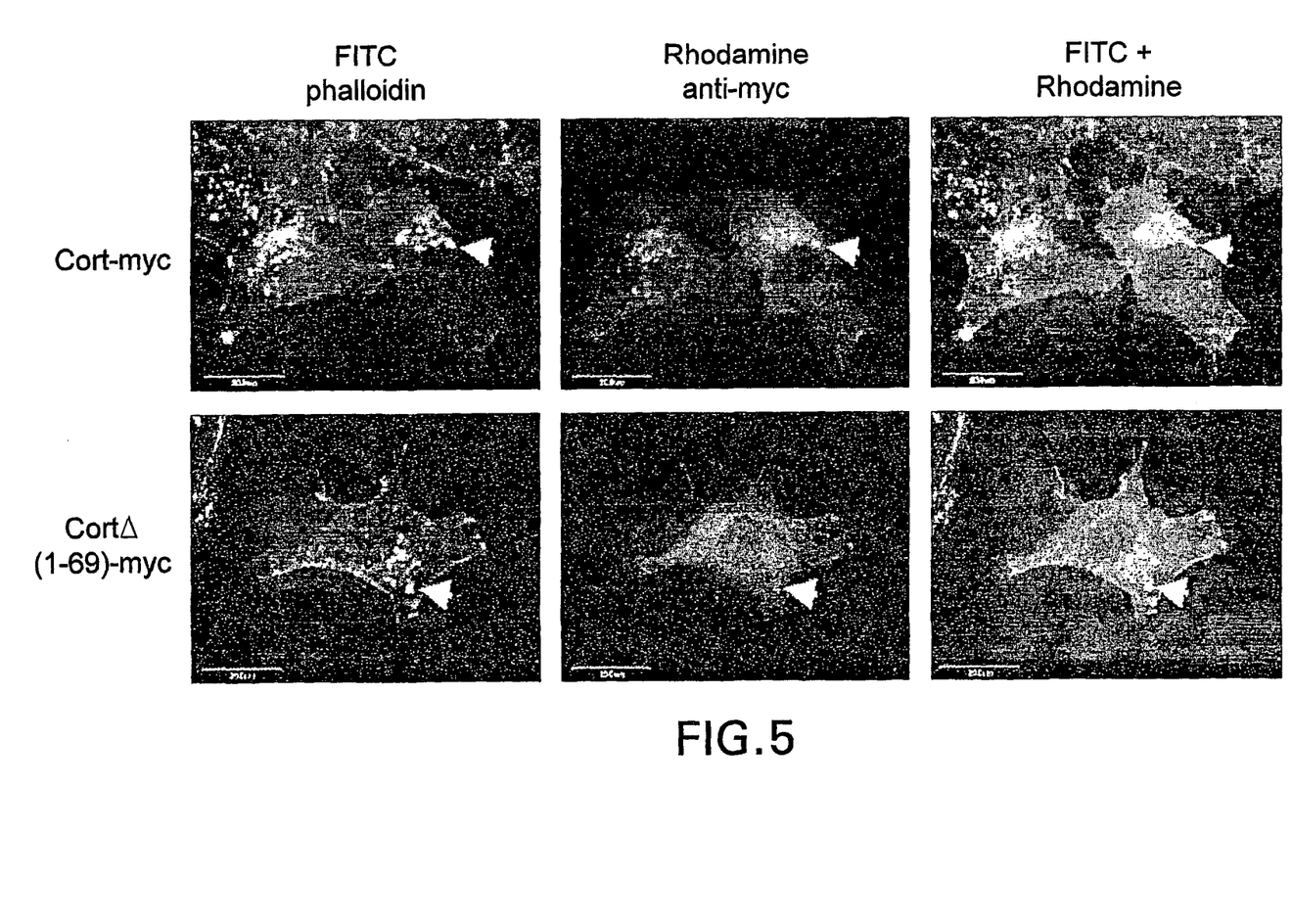
FIG. 5. Plasmids encoding cortactin-myc and CortΔ (1–69)-myc were transiently transfected into MDA-MB-231 cells grown at log-phase and plated on fibronectin-coated glass cover slips. After two days of transfection, the cells were fixed and stained with 9E-10 antibody for the myc epitope or with FITC-phalloidin for F-actin and examined by confocal microscopy.

To evaluate the function of the interaction of Arp2/3 complex with cortactin within cells, the distribution of cortactin in human MDA-MB-231 breast cancer cells was analyzed. MDA-MB-231 cells contain few stress fibers as analyzed by phalloidin staining (FIG. 5). Instead, they deposit most F-actin into large particulate structures that are associated with membrane. Within these particulate structures, endogenous cortactin (data not shown) or a wild-type cortactin tagged by myc epitope is accumulated (FIG. 5). In contrast to wild-type cortactin, a cortactin mutant with deletion of amino acids from 1 to 69 diffused within the cytoplasm and failed to localize within the F-actin-enriched particulate structures. Previous studies have demonstrated that cortactin is accumulated within invadopodium, a cortical particulate protrusion on the ventral side of cells that is implicated in the degradation of and penetration into the extracellular matrix, when MDA-MB-231 cells are plated on extracellular matrix (Bowden, E. T., et al., *Oncogene* 18:4440–4449 (1999)). Interaction with Arp2/3 complex is therefore required for the association of cortactin with F-actin enriched particulate protrusions of breast cancer cells.

Actin and cortactin-enriched particulate structures are also abundant in other types of cells such as osteoclasts (Hiura, K., et al., *Cell Motil. Cytoskeleton* 30:272–284 (1995)). In osteoclasts, these structures are called as podosomes and used to seal off a region of bone where resorption of bone occurs (Blair, H. C., et al., *Science* 245:855–857 (1989)).

Thus, Arp2/3 complex and cortactin mediated actin polymerization play a general role in the formation of dynamic cellular particulate structures by which cells interact with either extracellular matrix or other cells where extensive proteolysis takes place. It is also known that cortactin binds to several cellular proteins via either its phosphorylated tyrosine residues or the SH3 domain (Okumura, H., and Resh, M. D., *J. Biol. Chem.* 270:26613–26618 (1995); Takemoto, Y., et al., *EMBO J.* 14:3403–3414 (1995); Stevenson, B. R., et al., *J. Cell Biol.* 103:755–766 (1986); Ohoka, Y., and Takai, Y., *Genes Cells* 3:603–612 (1998); Du, Y., et al., *Mol. Cell Biol.* 18:5838–5851 (1998)). Hence, cortactin may link those proteins to the actin polymerization.

In light of the expression profile of cortactin, the discovery of the interaction of cortactin with Arp2/3 complex has a broad implications in other pathological processes in addition to tumor metastasis and osteoporosis. Abundant cortactin is also found within neural fibers, epithelial cells and megakaryocytes and platelets. Furthermore, tyrosine phosphorylation of cortactin is dramatically elevated in response to platelet agonists and reactive oxygen species, which play important roles in the development of thrombosis, hypertension, and atherosclerosis. Because these processes are intimately associated with the cytoskeletal changes, targeting at cortactin provides a new therapeutical approach to compromise these diseases.

Figure 6A:
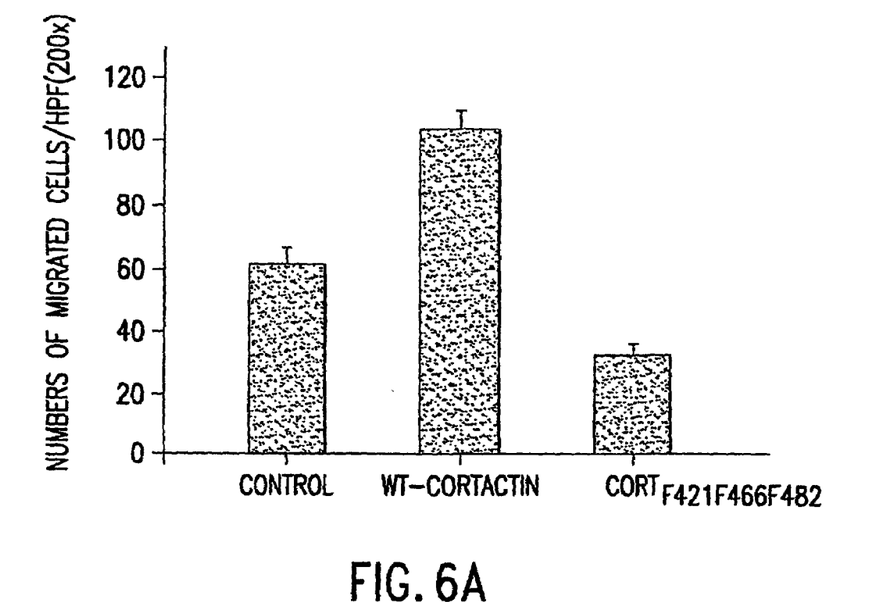
FIG. 6A shows a comparative histogram for the transendothelial migration of MDA-MB-231 cells expressing cortactin mutants. The numbers of migrated cells after 20 h is shown. The numbers reflect the mean±standard deviation of three independent experiments.

In order to examine the potential role of cortactin in pathogenesis, several studies were initiated on MDA-MB-231 breast cancer cells that overexpress cortactin mutants, which included examining their potential for transendothelial invasion (De Bruyn, P. P., et al., *J Morphol.* 133:417–437 (1971)). Invasion is a necessary metastatic event for tumor cells to migrate from the blood circulation to new tissues and requires the ability of tumor cells to change shape and invade across the endothelial lining between blood vessel and peripheral tissues. In this example, transendothelial invasion of tumor cells was evaluated. MDA-MB-231 cells expressing cortactin mutants were seeded over confluent human bone marrow endothelial cells (HBMEC) grown in the top chamber of Transwell, a modified Boyden chamber apparatus. After 20 h, the cells that migrated through the endothelial layer on the membrane on the bottom chamber were inspected by fluorescence microscopy. The cellular migration was analyzed by counting three high power field digital images randomly taken at 200× magnification. The average of cell number and the standard derivation were calculated based on duplicated experiments. As shown in FIG. 6A, cells expressing the wild-type cortactin (wt-cortactin) increased transendothelial invasion about 40% compared to the control cells expressing the vector only, whereas invasion was decreased by 45% in cells expressing the cortactin mutant deficient in tyrosine phosphorylation ($Cort_{F421F466F482}$).

Figure 6B:
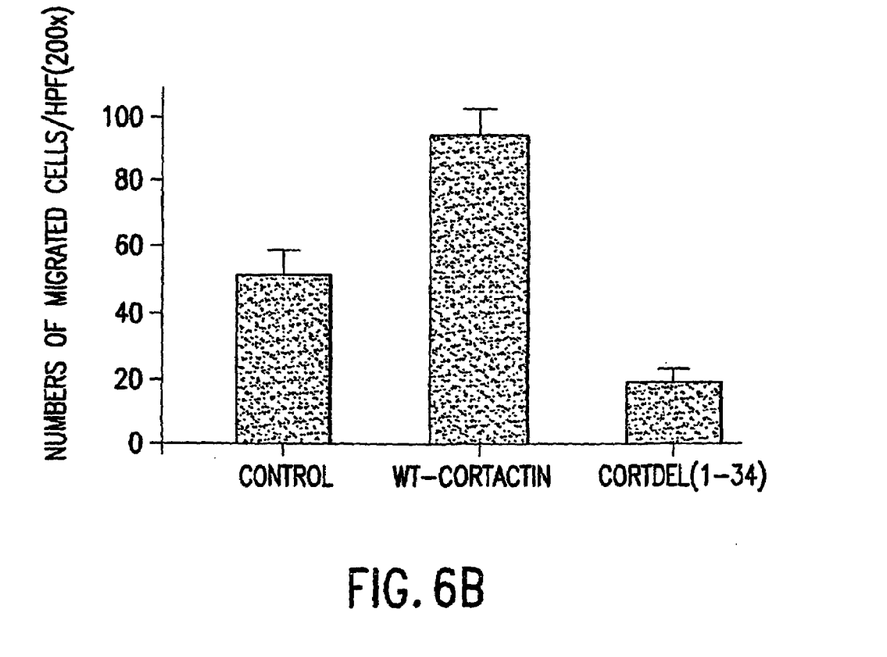
FIG. 6B shows a comparative histogram for the migration of MDA-MB-231 cells expressing cortactin mutants through a fibronectin-coated polycarbonate membrane. The numbers of migrated cells after 4 h is shown. The numbers reflect the mean±standard deviation of five independent experiments.

To further address the role of the interaction of cortactin with Arp2/3 complex in cell migration, a cortactin mutant was constructed containing a deletion of amino acids from 1 to 34 (Cortdel(1–34)), the region that is required for cortactin association with Arp2/3 complex. MDA-MB-231 cells expressing this cortactin mutation under the control of MGIN virus were evaluated for their motility using Transwell apparatus. Cells were seeded on a fibronectin-coated polycarbonate membrane insert in a Transwell and incubated in DMEM containing 10% FBS. After 4 h, the cellular migration was analyzed by counting five high power fields digital images randomly taken at 200× magnification. The average of cell number and the standard derivation were calculated based on duplicated experiments. The migration of was compared to the cells expressing wt-cortactin and the cells expressing the vector only. As shown in FIG. 6B, the cells expressing the mutation (Cortdel(1–34)) displayed 60% less migration through the membrane than the control cells. Thus, disruption of the interaction between cortactin and Arp2/3 complex effectively modulated cell migration. Cortactin mutant breast cancer cells deficient in either tyrosine phosphorylation (FIG. 6A) or Arp2/3 binding (FIG. 6B) demonstrated impaired motility as seen in Example 7.

Figure 7A:
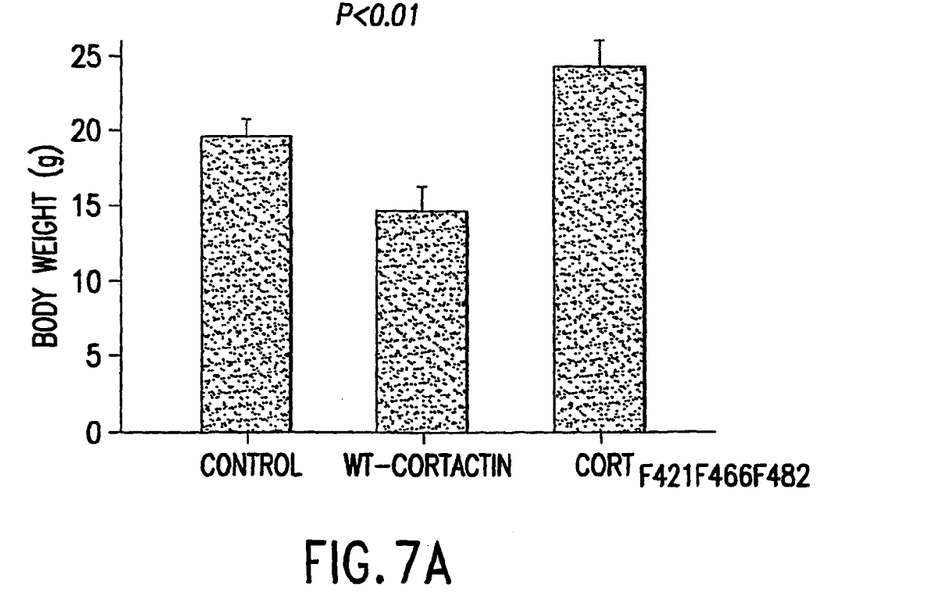
FIG. 7A shows the average body weight after 5 weeks for each test group.
Figure 7B:
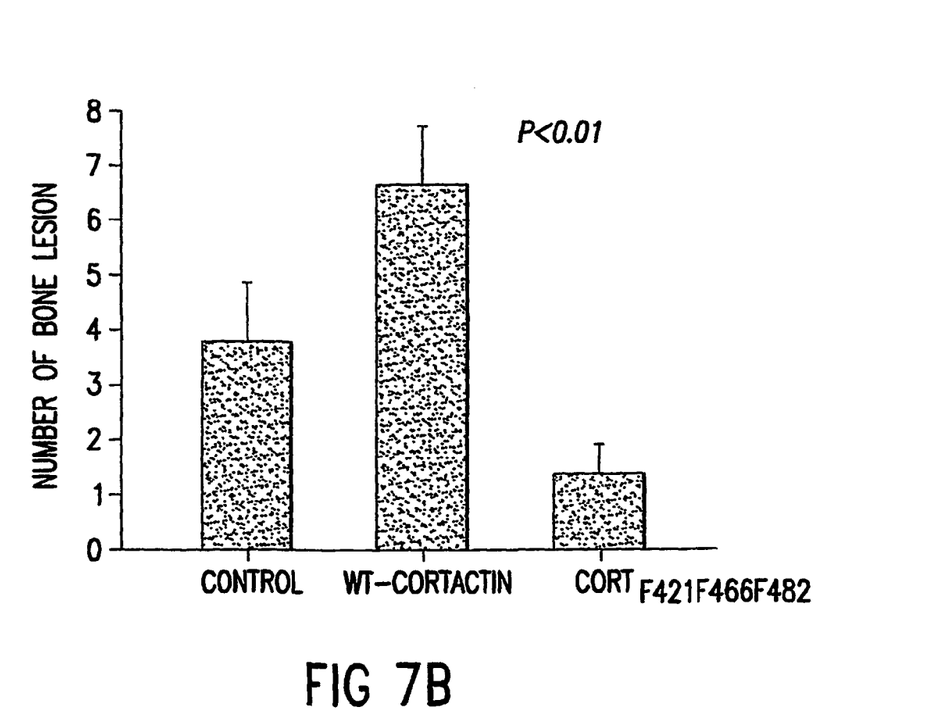
FIG. 7B shows the average number of bone lesions found in the test groups as analyzed by radiography. All data shown represent the mean±standard deviation (n=10). Representative radiography for each group is shown in FIG. 7C. Bone lesions at the joints between femurs and tibiae in high magnification are indicated by arrows in the bottom panel of FIG. 7C.
Figure 7C:
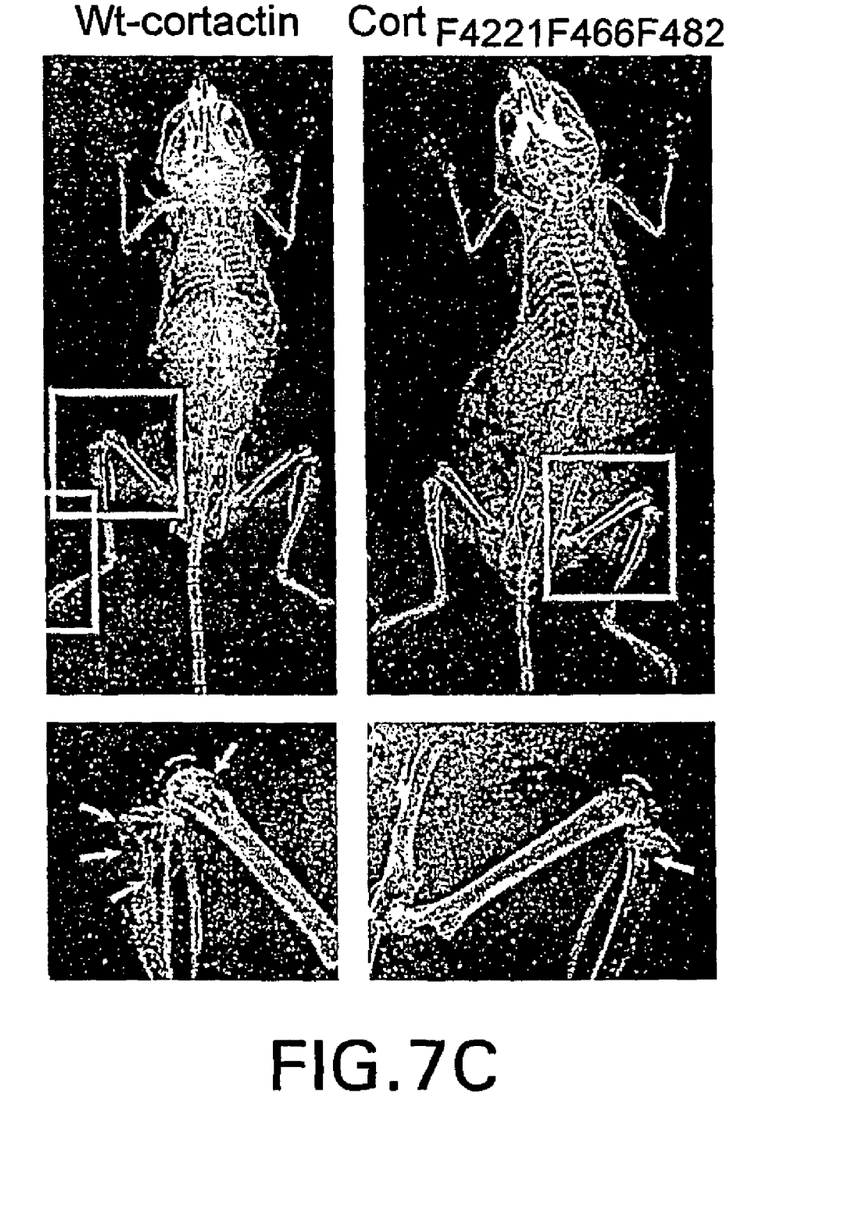

In order to examine whether cortactin mutants could interfere with tumor metastasis, an animal model for bone metastasis was employed in which MDA-MB-231 cells expressing cortactin mutants were injected into the left ventricles of nude mice (Mbalaviele, G. et al., *Cancer Res.* 56:4063–4070 (1996)). Five (5) weeks following the injection, the animals bearing wt-cortactin cells developed apparent cachexia (loss of muscle, fat, and body weight). These animals had an average body weight 25% less than that of control animals injected with cells expressing the viral vector only (FIG. 7A). In contrast, the average body weight of mice bearing $Cort_{F421F466F482}$ was about 20% higher than that of the control animals. Tumors that had metastasized into bone were examined by X-ray radiography, and revealed tumor-induced bone lesions as radiolucent foci (FIG. 7C). As summarized in FIG. 7B, the number of metastatic lesions present was approximately 15% of those seen in the control group. Further, mice bearing wt-cortactin cells developed an average of 7 tumors per animal, whereas the mice injected with $Cort_{F421F466F482}$ cells showed much less potential for bone metastasis with only one tumor per animal. This is consistent with previous findings that the mutation acts in a dominant negative manner within cells (Li, Y., et al., *J Biol. Chem.* 275:37187–93 (2000)), a result which confirms the function of cortactin in tumor metastasis.

The invention provides methods for screening for compounds which inhibit or activate actin polymerization. The invention is also directed to methods for screening for compounds which modulate the interaction between cortactin or HS-1 and Arp2/3. As used herein, it is understood that the term "cortactin" encompasses polypeptides which are at least 80% identical, 90% identical, preferably 95% identical, 96% identical, 97% identical, 98% identical or 99% identical to the amino acid sequence of cortactin. As used herein, it is understood that the term "HS-1" encompasses polypeptides which are at least 80% identical, 90% identical, preferably 95% identical, 96% identical, 97% identical, 98% identical or 99% identical to the amino acid sequence of HS-1.

As used herein, "an inhibitor of the interaction of cortactin or HS-1 with Arp2/3" is a compound which weakens or blocks the interaction of cortactin or HS-1 with Arp2/3. As used herein, "an enhancer of the interaction between cortactin or HS-1 and Arp2/3" is a compound which promotes or strengthens the interaction of cortactin with Arp2/3.

The interaction between cortactin or HS-1 and Arp2/3 in the presence of the compound which is being screened can be assayed by any of the methods and techniques known to those skilled in the art. Such methods include the pull-down assay (Uruno et al., *Nature Cell Biology* 3:259–266 (2001)), immunofluorescence, immunoprecipitation, gel migration analysis, radioisotopic tracer analysis and enzyme-linked immunosorbent assay (ELISA). A preferred assay technique is the pull-down assay.

Actin exists in three forms within cells: G-actin (monomeric actin), stress fibers (cross-linked actin filaments) and cortical acin (branched actin filaments). In response to extracellular signals, actin is rapidly polymerized from G-actin into cortical actin filaments. Because cell movement is the reflection of the extension on lamellipodia, the rate of the polymerization of cortical actin constitutes an important limit step for cell migration and cell shape changes. Accordingly, a preferred assay technique for use in the present invention is placing fluorescent labeled monomeric actin in polymerization buffer (10 mN Tris buffer, pH 7.5, containing 1 mM EGTA, 0.1 mM $CaCl_2$, 0.5 mM dithiothreitol, and 0.2 mM ATP), then initiating polymerization by adding 50 mM KCl and 1 mM $MgCl_2$. Polymerization can be measured, for example, by monitoring the increase in fluorescence of the fluorescent label.

As used herein, "fluorescent label" includes any molecule suitable to enable the detection of the interaction between cortactin or HS-1 and Arp2/3 in the presence of a compound which is being screened. An example of such a fluorescent label is pyrene. Other suitable fluorescent labels will be apparent to one of ordinary skill in the art. An increase in the rate of fluorescence (arbitrary units (au) per unit time) or intensity of fluorescence in the presence of cortactin or HS-1, Arp2/3 and the screened compound can be an indication that the screened compound is an enhancer of the interaction between cortactin or HS-1 and Arp2/3. A decrease or absence of fluorescence in the presence of cortactin or HS-1, Arp2/3 and the screened compound can be an indication that the screened compound is an inhibitor of the interaction between cortactin or HS-1 and Arp2/3.

As used herein, "administering" may be read so as to encompass all methods of delivery of a pharmaceutic agent known to one of skill in the art, also to encompass compounds which, when metabolized or degraded, produce the desired effect.

The invention is also drawn to compounds which modulate the interaction of cortactin or HS-1 with Arp2/3. The invention is also drawn to cortactin mutants or HS-1 mutants which are deficient in binding to Arp2/3.

An example of a method of screening for a cortactin inhibitor is examination of co-localization of Arp2/3 and cortactin proteins in mammalian cells. Arp2/3 and cortactin proteins can be in situ detected within cells by immunofluorescent staining using antibodies specifically against Arp2/3 and cortactin. Alternatively, mammalian cells can be transfected with plasmids or viral vectors carrying DNA fragments encoding cortactin proteins tagged with epitopes such as GFP, myc or HA. Thus, the subcellular localization of cortactin can be determined by staining cells with fluorescent-labeled antibodies against these epitopes.

Examples of inhibitors of actin polymerization encompassed by the present invention include compounds which bind to F-actin, but not Arp2/3, and compounds which bind to Arp2/3, but not F-actin. Such compounds may be determined empirically by one skilled in the art using routine screening methods.

Examples of inhibitors of the interaction of cortactin or HS-1 and Arp2/3 encompassed by the present invention include compounds which interact with the N-terminal domain of cortactin or HS-1, which is rich in acidic amino acids. Such compounds may be determined empirically one by skilled in the art using routine screening methods.

Examples of enhancers of actin polymerization encompassed by the present invention include compounds which bind to F-actin, but not Arp2/3, and compounds which bind to Arp2/3, but not F-actin. Such compounds may be determined empirically by one skilled in the art using routine screening methods.

Examples of enhancers of the interaction of cortactin or HS-1 and Arp2/3 encompassed by the present invention include compounds which interact with the N-terminal domain of cortactin or HS-1, which is rich in acidic amino acids. Such compounds may be determined empirically one by skilled in the art using routine screening methods.

Compounds which inhibit actin polymerization and/or compounds which inhibit the interaction of cortactin or HS-1 with Arp2/3 can be employed to treat tumor metastasis. Cortactin is often overexpressed in malignant tumors and in accumulated in invasopodia, a structure for cells to penetrate into the extracellular matrix.

Compounds which inhibit of actin polymerization and/or compounds which inhibit the interaction of cortactin or HS-1 with Arp2/3 can be employed to treat osteoporosis. Cortactin is enriched in the membrane protrusions of osteoclasts, which are used for the resorption of bone tissues. It is also known that mice deficient in Src can develop osteoporosis symptoms because they fail to form those protrusion structures in osteoclasts. Formation of these structures is known to require actin polymerization, which requires the function of cortactin. Interruption of the activity of cortactin will inhibit the activity of osteoclasts to resorb bone tissues and ultimately compromise osteoporosis.

Compounds which inhibit actin polymerization and/or compounds which inhibit the interaction of cortactin or HS-1 with Arp2/3 can be employed to inhibit angiogenesis. Recent studies have shown a critical role of Src in angiogenesis, which requires the migration of endothelial cells and degradation of extracellular basement membrane. Inhibition of cortactin will inhibit angiogenesis as well.

Compounds which inhibit actin polymerization and/or compounds which inhibit the interaction of cortactin or HS-1 with Arp2/3 can be employed to treat thrombosis. Cortactin is highly expressed in platelets and megakaryocytes. Tyrosine phosphorylation of cortactin in response to platelet agonists is a well-characterized and profound phenomenon, which is believed to promote actin cytoskeleton reorganization. Because tyrosine phosphorylation of cortactin occurs prior to the activation of integrins on the surface of platelets, the cortactin-mediated actin reorganization may play an important role for platelet aggregation. Inhibition of cortactin is expected to decrease the response of platelets to these agonists.

Compounds which enhance actin polymerization and/or compounds which enhance the interaction of cortactin or HS-1 with Arp2/3 can be employed to improve wound healing. Enhancement of cortactin's activity is expected to enhance cell migration, which is essential for healing of ulcers or wounds.

Compounds which enhance actin polymerization and/or compounds which enhance the interaction of cortactin or HS-1 with Arp2/3 can be employed to promote neurogenesis. Cortactin is enriched in the neuron fibers where actin polymerization is a key event in the neurite grown. The drugs that enhance the activity of cortactin should promote the growth of neurons and may potentially compromise neuron degeneration-related diseases such as Alzheimer's disease.

In accordance with another embodiment of the present invention there are provided methods of treating and processes of administering compounds to a host which would enhance actin polymerization and/or enhance the interaction of cortactin or HS-1 with Arp2/3 which are useful in stimulating wound healing and neurogenesis. Provided by the present invention is a method of promoting wound healing and neurogenesis in a mammal in need thereof comprising administering to a mammal in need thereof a therapeutically effective amount of a compound which would enance actin polymerization and/or enhance the interaction of cortactin or HS-1 with Arp2/3.

In accordance with still another embodiment of the present invention there are provided methods of treating a subject in need of treatment comprising administering to a subject a therapeutically effective amount of a compound which would inhibit actin polymerization and/or inhibit the interaction of cortactin or HS-1 with Arp2/3 which are useful in preventing or treating tumor metastasis, osteoporosis, angiogenesis and thrombosis. Preferably, the tumor metastasis is tumor metastasis of breast cancer cells. Preferably, the subject in need of treatment is a mammal. Preferably, the mammal is a human.

Also provided by the present invention is a mutant of cortactin, wherein the mutant confers to tumor cells about 0% to about 50% decreased ability to invade transendothelial cells when compared to the wild type cortactin derived from breast cancer cells. Preferably, said mutant confers to tumor cells from about 5% to about 45% decreased ability to invade transendothelial cells when compared to the wild type cortactin derived from breast cancer cells. More preferably, said mutant confers to tumor cells from about 10% to about 35% decreased ability to invade transendothelial cells when compared to the wild type cortactin derived from breast cancer cells. Even more preferably, said mutant confers to tumor cells from about 20% to about 25% decreased ability to invade transendothelial cells when compared to the wild type cortactin derived from breast cancer cells.

The compounds which modulate actin polymerization and/or enhance the interaction of cortactin or HS-1 with Arp2/3 can be employed in combination with any of the pharmaceutical carriers known to those skilled in the art. Such compositions generally comprise a therapeutically effective amount of the compound and a pharmaceutically acceptable carrier or exipient. Such a carrier includes but is not limited to saline, buffered saline, dextrose, water, glycerol, ethanol, and combinations thereof. The formulation employed should suit the mode of administration. Suitable formulations may be determined empirically by one skilled in the art.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered by any of the methods and routes known to those skilled in the art, including topical, intravenous, intraperitoneal, intramuscular, subcutaneous, intranasal or intradermal. The pharmaceutical compositions are preferably administered in an amount of at least about 10 mg/kg body weight and in most cases they will be administered not in excess of about 8 mg/Kg body weight per day. Most preferably, the dosage is from about 1 mg/Kg to about 10 mg/Kg body weight daily, taking into account the routes of administration, symptoms, etc.

EXAMPLES

Example 1

Preparation of Arp2/3 Complex

Bovine Arp2/3 complex was purified by a modified procedure as described previously (Egile, C., et al., *J. Cell Biol.* 146:1319–1332 (1999)). Briefly, 100 g of frozen bovine brain was minced with a Waring blender in 100 ml of 20 mM Tris, pH 8.0, containing 100 mM NaCl, 5 mM $MgCl_2$, 5 mM EGTA and 1 mM DTT (buffer Q) supplemented with 50 µg/ml phenylmethylsulfonyl fluoride, 5 µg/ml leupeptin and 1 µg/ml aprotinin. The minced tissue was further homogenized by a Dounce homogenizer and clarified by centrifugation at 40,000×rpm for 60 min at 4° C. The supernatant was subjected to chromatography in a 100 ml Sepharose Q column equilibrated with buffer Q. The flow-through containing Arp2/3 complex was collected, supplemented with 0.1 mM ATP and fractionated on a GST-N-WASP glutathione Sepharose column equilibrated with 50 mM Tris, pH 7.5, containing 25 mM KCl, 1 mM $MgCl_2$, 0.5 mM EDTA, 1 mM DTT and 0.1 mM ATP (buffer B). After washing with 0.2 M KCl in buffer B, the Arp2/3 complex was eluted with buffer B containing 0.2 M $MgCl_2$. The protein was then dialyzed against buffer B and concentrated by a Centriprep 10 cartridge. The concentrated Arp2/3 complex was stored in buffer B containing 30% glycerol at −80° C. Protein concentration was determined by the Bradford method (Bio-Rad protein Assay; Bio-Rad) using bovine gamma globulin as a standard. Concentrations at mg/ml were converted to molar concentrations based on the equivalence of 1 mg/ml to 18 µM cortactin, 23 µM actin, and 4.8 µM Arp2/3 complex.

Example 2

Analysis of Interaction of Arp2/3 Complex and Cortactin

Glutathione Sepharose conjugated with GST or GST-cortactin was mixed with 10 pmol of purified Arp2/3 complex in 100 µl of 50 mM Tris, pH 8.0, containing 150 mM NaCl, and 1% Triton X 100 (buffer A), and incubated for 2 h at 4° C. on a rotating wheel. The beads were rinsed three times with buffer A followed by boiling in 2×SDS sample buffer. Arp2/3 complex was detected by immunoblotting using a polyclonal Arp3 antibody after resolving by SDS-polyacrylamide gel electrophoresis. Data is shown in FIG. 2.

Example 3

In Vivo Interaction Assays

NIH 3T3 cells were lysed in buffer A supplemented with a protease inhibitor cocktail, and clarified by centrifugation at 14,000×rpm for 10 min at 4° C. The supernatants were immunoprecipitated with 20 µl of protein G-Sepharose with and without 2 µg of cortactin monoclonal antibody 4F11. The resulting immunoprecipitates were washed twice with buffer A, dissolved in 2×SDS sample buffer and subjected to SDS-PAGE followed by immunoblotting with Arp3 antibody, shown in FIGS. 2A and 2B.

Example 4

Construction of Cortactin Mutants

Deletion cortactin mutants, CortΔ(1–23), CortΔ(1–38), CortΔ(1–68), Cort(1–39), Cort(1–69), and Cort(1–80), were generated by PCR mutagenesis using the murine cortactin cDNA (pXZ112) as a template (Zhan, X., et al., *J. Biol. Chem.* 268:24427–24431 (1993)) with PfuTurbo polymerase (Stratagene). Point mutants Cort(W22A) and Cort (D20GD21A) are generated by site-directed mutagenesis using the Quickchange site-directed mutagenesis kit (Stratagene). All the constructs used herein, except for the three-repeat deletion mutant (pCH81), were first generated as the EcoRI-Sal 1 fragments then further, sub-cloned into the pUC19 plasmid. The resulting plasmids served as the master plasmids, from which the inserts were excised and further cloned into either the pGEX4T-2 (Amersham Pharmacia) for bacterial GST-fusion protein expression, or the pCMV-Tag5B plasmid (Stratagene) for mammalian expression of C-terminal myc-tagged proteins. The inserts in the master plasmids were verified by DNA sequencing. Comparison of exemplary mutants generated by this procedure may be seen at FIG. 3. The referenced numbers used are based on the amino acid sequence of murine cortactin (Zhan, X., et al, *J. Biol. Chem.* 268:24427–24431 (1993)).

Example 5

Actin Polymerization

Pyrene-labeled monomeric actin at concentration of 2.8 µM was incubated at 22° C. in polymerization buffer (10 mM tris buffer, pH 7.5, containing 1 mM EGTA, 0.1 mM $CaCl_2$, 0.5 mM dithiothreitol, and 0.2 mM ATP). Polymerization was initiated by adding KCl and $MgCl_2$ to final concentrations of 50 mM and 2 mM respectively, and monitored by measuring the increase in pyrene fluorescence using a LS50B spectrophotometer (Perkin Elmer) with filters for excitation at 365 nm and emission at 407 nm (15 nm and 10 nm band width, respectively). Data shown in FIG. 4 are the representatives of 2–4 experiments with identical results.

Example 6

Fluorescence Microscopy

MDA-MB-231 cells were transiently transfected with plasmids encoding cortactin-myc proteins with a Superfect transfection kit according to the manufacturer's protocol. The cells were plated on a glass cover slip pre-coated with fibronectin. After 24 hours, cells were fixed with 10% formaldehyde in PBS for 10 minutes and permeabilized with 0.5% Triton X-100 for 5 minutes. The treated cells were incubated for 1 h with a monoclonal anti-myc antibody (9E10) at the concentration of 2 µg/ml in PBS containing 5% BSA and then with a rhodamine-conjugated goat anti-mice antibody at 14 µg/ml in the same buffer for 30 minutes. For F-actin staining, fluorescein isothiocyanate-labeled phalloidin was added at a final concentration of 1 µM. Between each step, three-time washes with PBS were performed. The stained cells were finally mounted and examined under an Olympus Fluoroview confocal microscope using 0.60×/1.4 N.A. lens as shown in FIG. 5.

Example 7

Transendothelial Invasion and Cell Migration

Transendothelial invasion of MDA-MB-231 cells was analyzed based on a modified method as described (Okada, T., et al., *Clin. Exp. Metastasis* 12:305–314 (1994)). Briefly, human bone marrow endothelial cells ($3 \times 10^5$) were plated on a fibronectin-coated polycarbonate membrane insert (with 6.5 mm in diameter and 8.0 µm pores) in a Transwell apparatus. After cells reached confluence, MDA-MB-231 cells expressing wt-cortactin variants were trypsinized and resuspended in DMEM containing 10% FBS. The suspended cells ($3 \times 10^4$) were seeded in a monolayer of endothelial cells and incubated for 20 h at 37° C. in a $CO_2$ incubator.

For cell migration analysis, tumor cells were directly plated on fibronectin coated polycarbonate insert and incubated for 4 hours. After incubation, the insert was washed with PBS. The cells on the upper surface of the insert were removed by wiping with a cotton swab. The cells migrated to the lower surface of the insert were fixed with 3.7% formaldehyde and subjected to fluorescence microscopic inspection. Green cells were counted based on five HPF digital images randomly taken at 200× magnification. The average of cell number and the standard derivation were calculated based on duplicated experiments. Results are shown in FIG. 6.

Example 8

Intracardiac Injections of MDA-MB-231 Cells into Nude Mice

Subconfluent MDA-MB-231 cells were maintained in DMEM containing 10% FBS 24 h before injection. The cells were trypsinized, immediately suspended in DMEM containing 0.2 mg/ml soybean trypsin inhibitor, and washed twice with PBS. The washed cells were finally resuspended in cold PBS at a density of $2.5 \times 10^6$ cells/ml on ice. Female BALB/c-nu/nu mice at ages of 4 to 5 weeks (National Cancer Institute, Frederick, Md.) were anesthetized. MDA-MB-231 cells ($5 \times 10^5$) expressing wild-type or mutant cortactin protein were injected into the left ventricle of the animals. For each cell sample, 10 animals were analyzed. At 5 weeks after injection, the body weights of the mice were measured and the mice further examined by X-ray radiograph. FIG. 7 presents an analysis of bone metastases of MDA-MB-231 cells in the subject animals. All data shown represent the mean ± standard deviation (n=10). A representative radiograph is also shown. The bone lesions at the joints between femurs and tibiae in high magnification are indicated by arrows in the bottom panel.

All patents and publications referred to herein are hereby expressly incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An in vitro method of screening a compound for its ability to inhibit the interaction between cortactin and ARP2/3, said method comprising
    a. bringing a cortactin, ARP2/3 and a test compound into contact with one another in presence of one or more forms of actin; and
    b. detecting a decrease in polymerization activity of said actin in the presence of said test compound as compared to the polymerization activity of said actin in the absence of said test compound,
   wherein said decrease in polymerization activity of said actin indicates that said test compound inhibits the interaction between cortactin and ARP2/3.

2. The method of claim 1, wherein said one or more forms of actin is selected from the group comprising G-actin, cortical actin and cross-linked actin.

3. The method of claim 2, comprising at least two of said forms of actin.

4. The method of claim 3, wherein said detection comprises an immunoprecipitation assay.

5. The method of claim 3, wherein said detection comprises the use of a fluorescent label.

6. The method of claim 3, wherein said detection comprises an immunofluorescence assay.

7. The method of claim 3, wherein said detection comprises gel migration analysis.

8. The method of claim 3, wherein said detection comprises a radioisotopic tracer analysis.

9. The method of claim 3, wherein said detection comprises an enzyme-linked immunosorbent assay (ELISA).

* * * * *